United States Patent [19]

Grebinoski et al.

[11] Patent Number: 5,352,839
[45] Date of Patent: Oct. 4, 1994

[54] ISOPHORONE PROCESS

[75] Inventors: Michael C. Grebinoski, West Deer Township, Allegheny County; Donald Glassman, Mt. Lebanon Township, Allegheny County; Carole L. Elias, New Kensington; Alain A. Schutz, Penn Township, Westmoreland County, all of Pa.

[73] Assignee: Aristech Chemical Corporation, Pittsburgh, Pa.

[21] Appl. No.: 118,341

[22] Filed: Sep. 9, 1993

[51] Int. Cl.$^5$ .............................................. C07C 45/82
[52] U.S. Cl. ................................... 568/366; 568/353
[58] Field of Search ..................... 568/353, 360, 366

[56] References Cited

U.S. PATENT DOCUMENTS

| | | | |
|---|---|---|---|
| 3,337,633 | 8/1967 | Schmitt et al. | 260/586 |
| 3,981,918 | 9/1976 | Walton et al. | 260/586 C |
| 4,059,632 | 11/1977 | Cane et al. | 260/586 C |
| 4,165,339 | 8/1979 | Reichle | 260/586 |
| 4,434,301 | 2/1984 | Papa | 568/366 |
| 4,458,026 | 7/1984 | Reichle | 502/80 |
| 4,535,187 | 8/1985 | Papa et al. | 568/353 |
| 4,970,191 | 11/1990 | Schutz | 502/341 |
| 5,055,620 | 10/1991 | Schutz | 568/353 |
| 5,153,156 | 10/1992 | Schutz et al. | 502/63 |

FOREIGN PATENT DOCUMENTS

| | | | |
|---|---|---|---|
| 1000574 | 8/1965 | United Kingdom | 568/366 |
| 1265029 | 3/1972 | United Kingdom | 568/366 |

OTHER PUBLICATIONS

Salvapati et al., "Selective Catalytic Self–Condensation of Acetone", Journal of Molecular Catalysis, 54(1989), pp. 9–30.

*Primary Examiner*—James H. Reamer
*Attorney, Agent, or Firm*—William L. Krayer

[57] ABSTRACT

Isophorone is made by the aldol condensation of acetone followed by separate steps to remove acetone, mesityloxide, and beta isophorone. Variations include recycling of mesityloxide and/or beta isophorone.

19 Claims, 3 Drawing Sheets

ISOPHORONE PROCESS

TECHNICAL FIELD

This invention relates to the manufacture of isophorone from acetone.

BACKGROUND OF THE INVENTION

Prior to the present invention, it has been known to make isophorone through the aldol condensation of acetone. However, the nuances, variations, and complications of this seemingly simple reaction may be tentatively appreciated by noting the summary of a paper by Salvapati, Ramanamurty, and Janardanarao (Journal of Molecular Catalysis, 54 [1989] 9–30): "Catalytic self-condensation of acetone is a very complex reaction and numerous products are possible via competitive self-condensation and cross-condensation between the same or different ketones that are formed in the reaction. All the major products of the reaction, diacetone alcohol, mesityloxide, phorone, mesitylene, isophorone, 3,5-xylenol and 2,3,5-trimethylphenol find important industrial applications. The reaction is catalysed by acids as well as bases, and it can be carried out in both liquid and vapour phases. The selectivity of the reaction for the desired product is achieved by proper choice of catalyst and experimental conditions. This paper reviews the recent developments in the process of self-condensation of acetone, evaluating the significance of various parameters for obtaining the desired product." The Salvapati et al article goes on to describe in some detail and with copious structural formulas the various possibilities in the autocondensation of acetone and the aromatization of isophorone, especially in the presence of acetone. It is clear that the catalyst and conditions for the aldol condensation of acetone must be carefully chosen to achieve a practical selectivity for isophorone.

This invention is designed to employ effectively a catalyst of the type described by Schutz in U.S. Pat. No. 4,970,191; preferably the catalyst is enhanced by the process of extruding or otherwise forming it described by Schutz and Cullo in U.S. Pat. No. 5,153,156. Methods of making isophorone described by Schutz in U.S. Pat. No. 5,055,620 and by Schutz and Cullo in U.S. Pat. No. 5,202,496 are also especially applicable to the present invention; use of the catalyst to react acetone in the vapor phase is particularly of interest in the present invention. The Schutz and Schutz/Cullo patents employ pseudoboehmite reacted with an acid to form a gel, to which is added magnesium oxide or hydroxide in particular ratios, followed by agitation, heating, and calcining. These patents are incorporated herein by reference in their entirety.

However, our invention may use also, or in place of the catalysts of the above-recited Schutz and Schutz/Cullo patents, a catalyst of the type disclosed by Reichle in U.S. Pat. No. 4,165,339 and 4,458,026 and/or Papa et al U.S. Pat. No. 4,535,187, to the extent they are practical. As mentioned below, this invention is a process for the vapor phase aldol condensation of acetone to make isophorone, and is intended to include the use of any catalyst which will catalyze such a reaction, including catalysts described in any of the above-cited patents which are known to do so, to the extent applicable.

SUMMARY OF THE INVENTION

We have developed an integrated process which advantageously uses the Schutz/Cullo catalyst (U.S. Pat. Nos. 5,153,156 and/or 4,970,191) or other catalysts mentioned above, as well as any other practical aldol condensation catalyst, in a manner which is efficient both in product yield and energy consumption and which is consistent with the methods of making isophorone disclosed in U.S. Pat. Nos. 5,055,620 and 5,202,496 to Schutz and Cullo. The energy savings are provided by a heat exchanger network which minimizes heat losses in an energy-intensive process. In addition, the recycle of various by-product streams, which either equilibrate or convert to the desired isophorone, serves to increase the overall process yield of isophorone from acetone.

In our process, fresh acetone is mixed with the various process recycle streams consisting primarily of acetone, mesityloxide, and isophorone. The resultant feed is partially vaporized preferably by heat exchange with the reactor outlet, then totally vaporized using steam or another suitable heating medium. The thus obtained vapor is superheated preferably by further heat exchange with the reactor outlet, and finally brought to an inlet or feed temperature of 225°–325° C. in a direct fired heater or other suitable heat source.

The superheated feed is reacted in the vapor phase to convert about 10 to 35% of the acetone, causing an adiabatic temperature rise of about 7° to 50° C. The reactor product is partially condensed, preferably by the aforementioned heat exchange with the reactor feed, thus recovering a large portion of the heat of reaction which, in the preferred version, in turn decreases the need for external energy sources. Unreacted acetone is then separated from the reaction products by distillation and recycled to the reactor. The bottoms product from the distillation column consists of an organic phase and an aqueous phase. The two phases are fed to a decanter or other phase separator after cooling by interchange with the decanter organic outlet. The organic phase is fed to another distillation column where the mesityloxide and remaining water are separated from the crude isophorone and then recycled to the reactor.

A further distillation is conducted in which the isophorone isomers, mainly beta isophorone and phorones, are separated from the product. The by-product mesitylene is removed in an overhead purge. The sidestream, which contains the isophorone isomers, is recycled to the reactor feed. Beta isophorone is the isomer illustrated in a structural formula as follows:

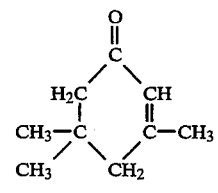

alpha-isophorone

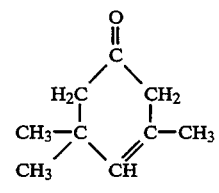

beta-isophorone

Although the beta isomer of isophorone (and phorone isomers) is generally less than about 10% of the alpha, at least under the conditions of our process, consistent removal of it has proven to be very beneficial to the color of the final product. The crude isophorone from the bottoms of the beta isophorone/phorone distillation is further purified in a final distillation column to remove heavy components. The resultant isophorone product has a purity of greater than 99%. Further improvement in the overall yield of the process can be realized by the optional stripping of the reaction water to recover acetone, mesityloxide, and isophorone to the extent that they are soluble in the reaction water. The recovered organics from the overhead of the stripper can be recycled to the acetone column.

Thus, our process is seen to comprise feeding acetone in the vapor phase at a temperature between about 225°–325° C. to an aldol condensation catalyst to convert about 10% to about 35% of the acetone to a reaction product containing about 4% to about 20% alpha isophorone, removing water and mesityloxide from said reaction product, and, in a separate isomer distillation, removing the beta form of isphorone, and phorone, from said reaction product. The isophorone product of >99% purity is recovered by removing the heavies in a final distillation step. Soluble acetone, mesityloxide, and isophorone may be recovered from the reaction water and recycled to the acetone column.

DETAILED DESCRIPTION OF THE INVENTION

Figure 1:
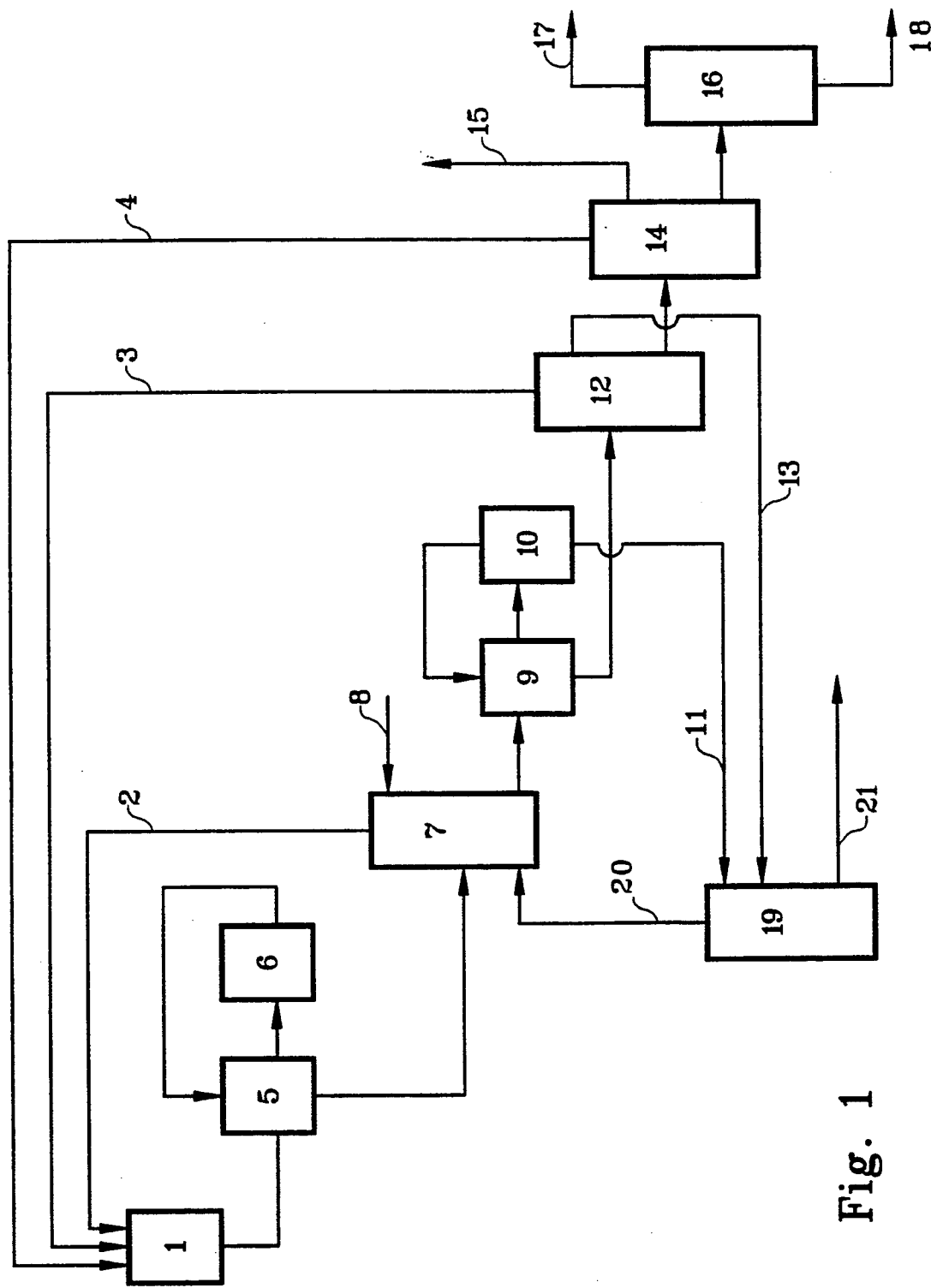
FIG. 1 is a block flow diagram or flow sheet of our process.

In FIG. 1, feed mixer 1 continuously receives acetone from line 2, and mixes it with recycled materials in lines 3, and 4 to be described. The mixture is heated, preferably by interchange 5 with the reactor outlet and directed to reactor 6 which is maintained initially at a temperature between 225°–325° C. and at a pressure to deploy the mixture in the vapor phase. The reactor contains a catalyst of the type described in the previously-cited Schutz/Cullo patents, in an amount to convert about 10–35% of the acetone in the feed, which will tend to increase the temperature in the reactor by about 7°–50° C. The active portion of the catalyst is preferably a synthetic anionic clay of the type described in lines 33–38 of column 3 of U.S. Pat. No. 5,153,156, namely of the formula $(Mg_{1-x}Al_x)(OH)_2 \cdot xA$ where x is a number from 0.1 to 0.5, A is a univalent organic anion of the formula $RCOO^-$, where R is $C_nH_{2n+1}$ and n is 0 to 4.

The reaction product (typically about 20% converted) is sent to the acetone distillation column 7 along with fresh acetone in line 8 and recovered organic feeds and products in line 20 to be described. Column 7 is operated at a pressure of 300 mmHg to 20 psig, preferably about 650 mmHg to 850 mmHg. After acetone removal, the resultant stream is two phase and is preferably fed to decanter 10 whereby the isophorone-rich organic layer is separated from the aqueous phase which contains most of the water formed in the reaction. The decanter feed is cooled by interchange with the decanter organic outlet in heat exchanger 9. In a less preferable mode, the two phases may be fed directly to the subsequent distillation; however, this will result in a large increase in energy requirements, thus reducing the overall energy efficiency of the process.

The decanted organic phase is then forwarded to the mesityloxide distillation column 12, where mesityloxide is removed for recycling through line 3 to feed mixer 1, and water is removed from the system in line 13. Column 12 operates at a pressure of about 100 mmHg to 20 psig, preferably about 400 to 600 mmHg. The reaction product continues to a beta distillation column 14, where beta isophorone and phorone isomers are removed for recycling through line 4 to feed mixer 1, and mesitylene and other light impurities are purged in line 15. Column 14 operates at a pressure of 20 mmHg to 600 mmHg, preferably 100–300 mmHg (about 5 psig). The bottoms from column 14, now comprising about 85% by weight of the desired alpha isophorone, are forwarded to a product distillation column 16, where it is purified to, preferably, at least 99% alpha isophorone, delivered from line 17 and heavies are purged in line 18. Column 16 operates at a pressure of 10 to 300 mmHg, preferably 50 to 100 mmHg (about 5 psig).

Water from line 11 and line 13 is sent to a stripping column 19, where organic components dissolved in the water are removed for recycling through line 20 to the acetone distillation column 7; waste water is removed in line 21.

Figure 2:
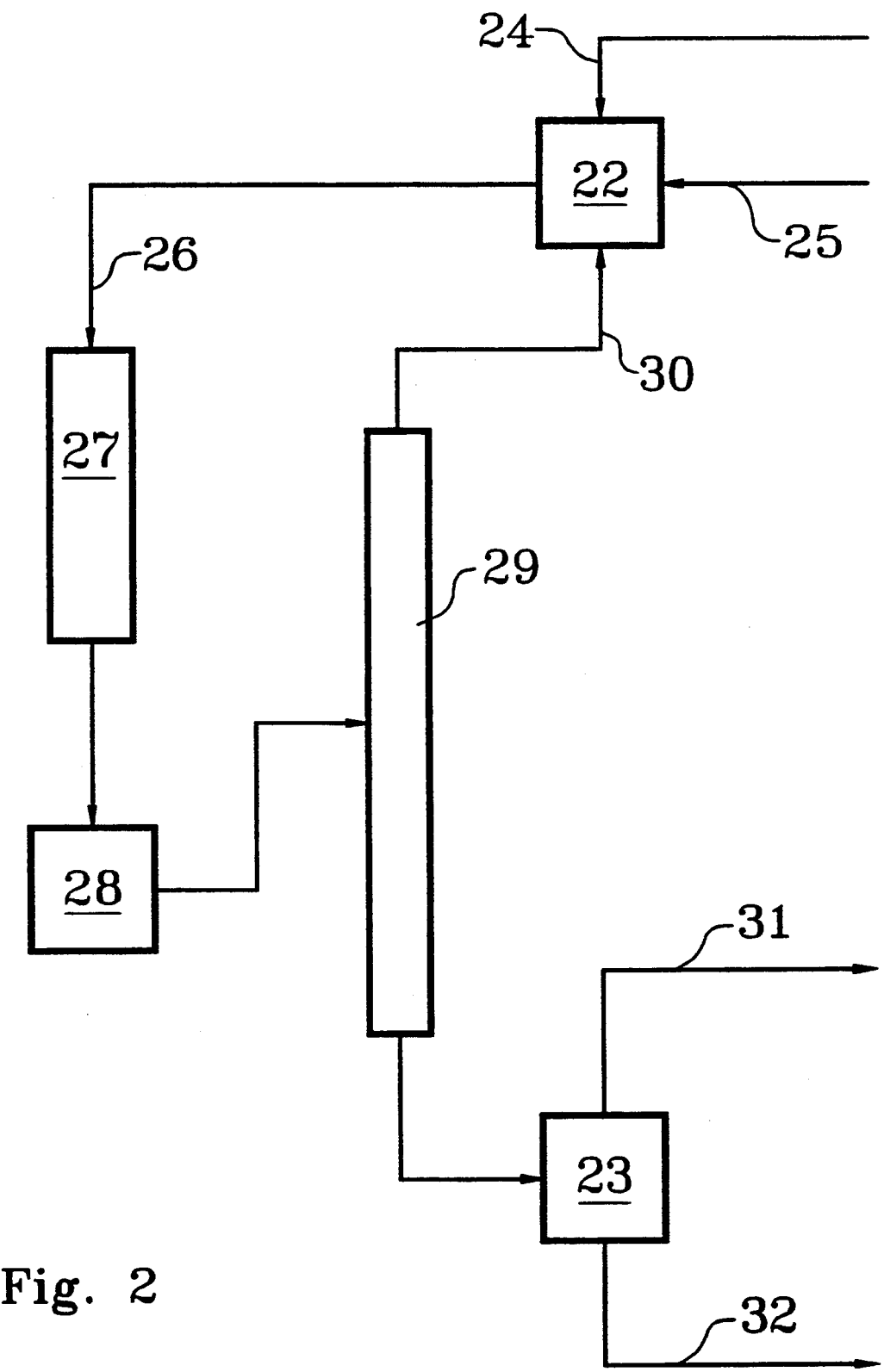
FIG. 2 is a block flow diagram of a pilot plant used to demonstrate the front end of the process.

The pilot plant of FIG. 2 was set up so that the feed tank 22 could receive unused acetone from line 25, and distilled acetone from line 30, and/or recycled products such as mesityloxide and isophorone isomers from line 24. The material contained in the feed tank 22 was pumped and vaporized through line 26 to the reactor 27 containing the catalyst, at a rate of about 665 g per hour. The reactor temperature was maintained at about 270° to 300° C. and the reactor pressure was about 15 psig. The reactor outlet stream was condensed and stored in tank 28 and subsequently pumped to the continuous column 29, which was an Oldershaw with 20 rectification trays, 8 stripping trays, maintained at 760 mmHg and with a reboiler temperature of 95° C. The overheads of the column, comprising acetone and water, were pumped back to feed tank 22. The bottoms of the column, comprising the reaction products, were separated in the decanter 23 into an organic phase (line 31) and an aqueous phase (line 32).

EXAMPLE 1

The data in Tables 1 and 2 were generated in the pilot configuration of FIG. 2. In Table 1, no mesityloxide or isophorone isomer$ were fed to the reactor; in Table 2, an approximation of the process described for FIG. 1 was conducted, i.e. the feed material contained both mesityloxide and isophorone isomers along with the acetone. It will be seen from Tables 1 and 2 that the presence of recycled mesityloxide in the feed does not affect the reaction product selectivities. In addition, the data show that the recycling of beta isophorone results in its isomerization to alpha isophorone without reacting or forming heavier condensation or other undesirable products. This is an important commercial factor, since the accumulation of beta isophorone will tend to result in an undesirable colored product. It was noted also that mesitylene tends to build up; after two weeks of recycling, its concentration increased from an initial 0.02 to 0.1 weight percent. Although it is not essential to do so, the process may be designed to purge the mesitylene, as in line 15 of FIG. 1. It may be calculated from Table 2 that each 100 parts of acetone was converted to 70.85 parts alpha isophorone, 20.37 parts water, and 8.76 parts heavies.

TABLE 1

Pilot plant data. Acetone feed with recycled acetone only. Hourly rates.

|  | reactor inlet | | reactor outlet | | acetone column overheads | | acetone column bottoms | | decanter: organic phase | | decanter: aqueous phase | |
| --- | --- | --- | --- | --- | --- | --- | --- | --- | --- | --- | --- | --- |
|  | (g) | (WT %) | (g) | (WT %) | (g) | (WT %) | (g) | (WT %) | (g) | (WT %) | (g) | (WT %) |
| ACETONE | 650.70 | 98.00% | 517.50 | 77.94% | 516.50 | 97.50% | 0.90 | 0.67% | 0.54 | 0.47% | 0.36 | 1.92% |
| MESITYL-OXIDE | 0.00 | 0.00% | 19.39 | 2.92% | 0.00 | 0% | 19.39 | 14.46% | 19.34 | 16.76% | 0.05 | 0.27% |
| MESITYLENE | 0.00 | 0.00% | 0.12 | 0.02% | 0.00 | 0% | 0.12 | 0.09% | 0.12 | 0.10% | 0.00 | 0.00% |
| β-ISOPH. | 0.00 | 0.00% | 4.26 | 0.64% | 0.00 | 0% | 4.26 | 3.18% | 4.25 | 3.68% | 0.01 | 0.05% |
| PHORONE | 0.00 | 0.00% | 0.15 | 0.02% | 0.00 | 0% | 0.15 | 0.11% | 0.15 | 0.13% | 0.00 | 0.00% |
| ISOPHORONE | 0.00 | 0.00% | 75.36 | 11.35% | 0.00 | 0% | 75.36 | 56.19% | 75.26 | 65.22% | 0.10 | 0.53% |
| C12 | 0.00 | 0.00% | 2.47 | 0.37% | 0.00 | 0% | 2.47 | 1.84% | 2.47 | 2.14% | 0.00 | 0.00% |
| C15 | 0.00 | 0.00% | 6.29 | 0.95% | 0.00 | 0% | 6.29 | 4.69% | 6.29 | 5.45% | 0.00 | 0.00% |
| TMT | 0.00 | 0.00% | 2.10 | 0.32% | 0.00 | 0% | 2.10 | 1.57% | 2.10 | 1.82% | 0.00 | 0.00% |
| HEAVIES | 0.00 | 0.00% | 0.88 | 0.13% | 0.00 | 0% | 0.88 | 0.66% | 0.88 | 0.76% | 0.00 | 0.00% |
| WATER | 13.28 | 2.00% | 35.52 | 5.35% | 13.30 | 2.50% | 22.20 | 16.55% | 4.00 | 3.47% | 18.20 | 97.22% |
| TOTAL | 663.98 | 100.00% | 664.00 | 100.01% | 529.80 | 1.00 | 134.12 | 100.00% | 115.40 | 100.00% | 18.72 | 100.00% |

TABLE 2

Pilot plant data. Acetone feed containing recycled mesityloxide, phorone and isophorones. Hourly rates.

|  | reactor inlet | | reactor outlet | | acetone column overheads | | acetone column bottoms | | decanter: organic phase | | decanter: aqueous phase | |
| --- | --- | --- | --- | --- | --- | --- | --- | --- | --- | --- | --- | --- |
|  | (g) | (WT %) | (g) | (WT %) | (g) | (WT %) | (g) | (WT %) | (g) | (WT %) | (g) | (WT %) |
| ACETONE | 617.77 | 93.08% | 515.64 | 77.70% | 514.64 | 97.50% | 0.90 | 0.67% | 0.54 | 0.46% | 0.36 | 1.94% |
| MESITYL-OXIDE | 21.00 | 3.16% | 20.30 | 3.06% | 0.00 | 0.00% | 20.30 | 15.03% | 20.25 | 17.37% | 0.05 | 0.27% |
| MESITYLENE | 0.50 | 0.08% | 0.66 | 0.10% | 0.00 | 0.00% | 0.66 | 0.49% | 0.66 | 0.57% | 0.00 | 0.00% |
| β-ISOPH. | 5.00 | 0.75% | 5.14 | 0.77% | 0.00 | 0.00% | 5.14 | 3.80% | 5.13 | 4.40% | 0.01 | 0.05% |
| PHORONE | 0.17 | 0.03% | 0.20 | 0.03% | 0.00 | 0.00% | 0.20 | 0.14% | 0.20 | 0.17% | 0.00 | 0.00% |
| ISOPHORONE | 6.00 | 0.90% | 76.49 | 11.53% | 0.00 | 0.00% | 76.49 | 56.60% | 76.39 | 65.50% | 0.10 | 0.54% |
| C12 | 0.00 | 0.00% | 2.19 | 0.33% | 0.00 | 0.00% | 2.19 | 1.62% | 2.19 | 1.88% | 0.00 | 0.00% |
| C15 | 0.00 | 0.00% | 5.93 | 0.89% | 0.00 | 0.00% | 5.93 | 4.38% | 5.93 | 5.08% | 0.00 | 0.00% |
| TMT | 0.00 | 0.00% | 0.43 | 0.06% | 0.00 | 0.00% | 0.43 | 0.32% | 0.43 | 0.37% | 0.00 | 0.00% |
| HEAVIES | 0.00 | 0.00% | 0.91 | 0.14% | 0.00 | 0.00% | 0.91 | 0.67% | 0.91 | 0.78% | 0.00 | 0.00% |
| WATER | 13.27 | 2.00% | 35.00 | 5.40% | 13.30 | 2.50% | 22.00 | 16.28% | 4.00 | 3.43% | 18.00 | 97.19% |
| TOTAL | 663.71 | 100.00% | 663.71 | 100.02% | 527.94 | 100.00% | 135.14 | 100.00% | 116.62 | 100.00% | 18.52 | 100.00% |

Figure 3:
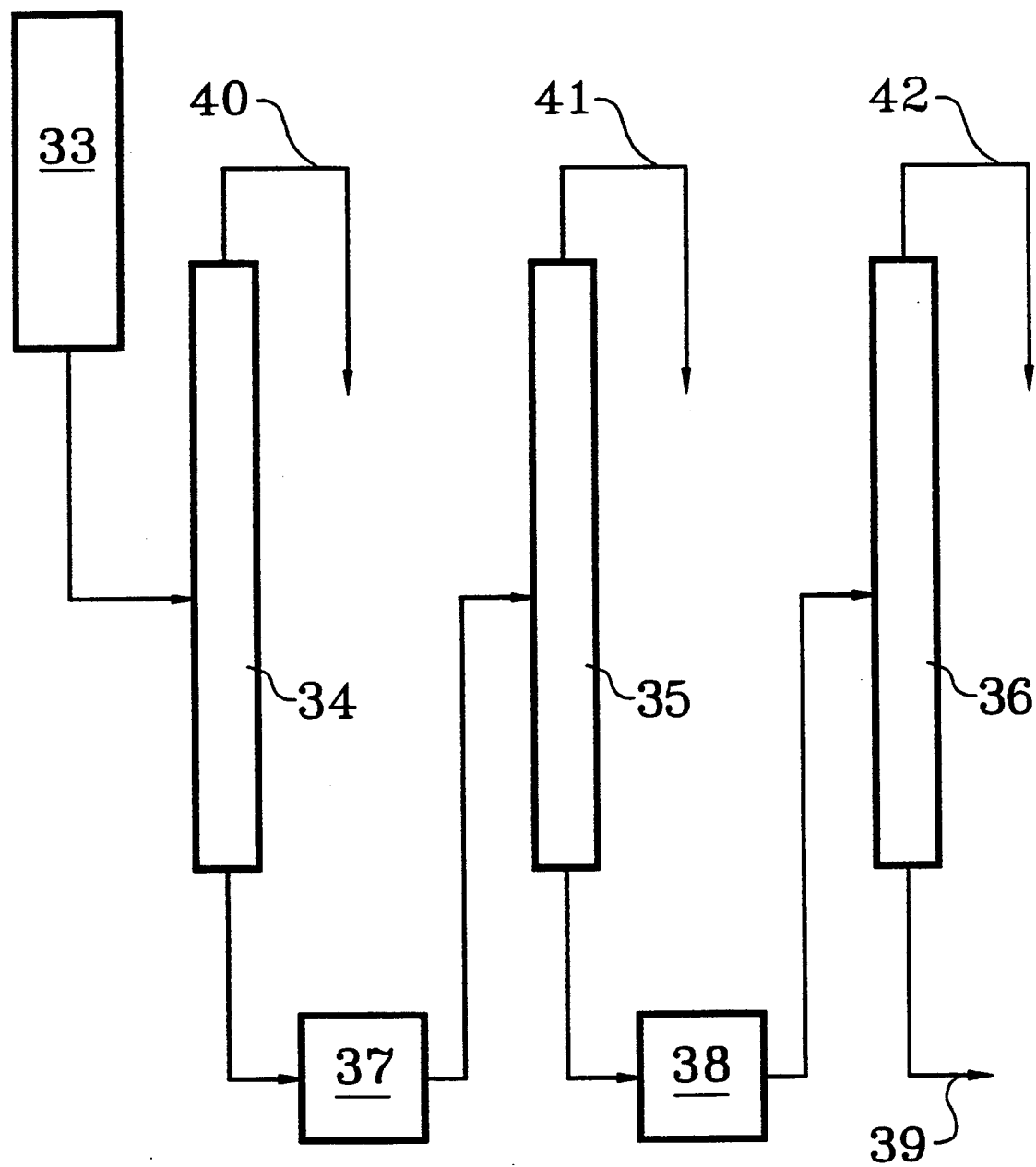
FIG. 3 is a block flow diagram of a pilot plant used to demonstrate the back end of our process.

The pilot plant of FIG. 3 was set up to simulate the "back end" of the plant. The organic phase from line 31 of FIG. 2, i.e. equivalent to the organic phase from the decanter 10 in FIG. 1, was stored in feed tank 33 and fed to the mesityloxide distillation column 34, equivalent to the first stage distillation unit 12 of FIG. 1, at a rate of about 525 ml/hr. This was a 1" Oldershaw having 5 rectification trays, 15 stripping trays, and operated at a top pressure of 400 mmHg, and a reboiler temperature of 193° C. Mesityloxide and some water are removed at the top of the column 34. The bottoms from column 34 were stored in tank 37 and then pumped to distillation column 35, equivalent to second stage distillation column 14 in FIG. 1; this was a 1" Oldershaw having 15 rectification trays, 30 stripping trays, and operated at a top pressure of 300 mmHg, and a reboiler temperature of 189° C. Most of the beta isophorone and phorones are removed overhead, and the bottoms from column 35 were stored in tank 38 and pumped to column 36 for purification of the product. Column 35, representing the third stage column 16 in FIG. 1, was a 1" Oldershaw having 20 stripping trays, 15 rectification trays, and operated at a top pressure of 70 mmHg, and a reboiler temperature of 188° C. The isophorone product was collected from line 42 and the heavies from line 39. Mesityloxide from line 40 and isophorone isomers from line 41 were recycled to the reaction section, i.e. reactor 27 in FIG. 2.

EXAMPLE 2

By using the experimental distillation train described and shown in FIG. 3, decanted organic material obtained from the front end of the process has been fractionated so that recycled streams and isophorone product were made. 3305 g were pumped from tank 33 of FIG. 3. 676 g of mesityloxide composite (including 95 g water) were collected from line 40, 212 g of beta isophorone overheads and 2510 g of beta bottoms were made. Analyses of these fractions are shown in Table 3.

TABLE 3 wt % analyses of distillation fractions.

| | Decanted Organics | Mesityloxide overheads | Beta overheads | Beta bottoms |
| --- | --- | --- | --- | --- |
| acetone | 0.86 | 5.20 | — | — |
| mesityl-oxide | 14.40 | 93.94 | 2.61 | — |
| mesitylene | 0.24 | 0.25 | 2.30 | — |
| beta isophorone | 4.15 | 0.07 | 60.36 | 0.06 |
| phorone | 0.14 | — | 21.8 | 0.02 |
| isophorone | 69.84 | 0.02 | 32.26 | 87.16 |
| c12 | 1.84 | — | 0.27 | 2.71 |
| c15 | 5.99 | — | — | 7.39 |
| tmt | 1.45 | — | — | 1.83 |
| heavies | 0.98 | — | — | 0.83 |

1364 g of beta bottoms were pumped into the product column. 1133 g of product (99.7% alpha isophorone, APHA color 10–15) was collected from line 42 and 231 g of a heavy fraction was recovered from line 39. Analyses of these fractions are shown in Table 4.

TABLE 4

| wt % analyses of product column fractions. | | |
| --- | --- | --- |
| | Isophorone overheads | Column bottoms |
| acetone | — | — |
| mesityloxide | — | — |
| mesitylene | — | — |
| beta isophorone | 0.12 | — |
| phorone | 0.01 | — |
| isophorone | 99.72 | 3.78 |
| c12 | 0.15 | 17.16 |
| c15 | — | 62.36 |
| tmt | — | 10.43 |
| heavies | — | 6.27 |

We claim:

1. Method of making isophorone comprising conducting an aldol condensation of acetone in the vapor phase in the presence of an aldol condensation catalyst at a temperature between about 225° C. to about 325° C. to obtain a reaction product in which at least about 10% of the acetone is converted, removing unreacted acetone in an acetone removal zone, removing free water from the reaction product, removing mesityloxide and water in a mesityloxide removal zone, thereafter removing beta isophorone and mesitylene from said reaction product in a beta isophorone and mesitylene removal zone, and purifying the remaining reaction product to obtain an end product of at least 99% purity.

2. Method of claim 1 wherein the acetone removal zone comprises a distillation column .

3. Method of claim 1 wherein the removal of free water is conducted in a decanter.

4. Method of claim 1 wherein the mesityloxide removal zone comprises a distillation column.

5. Method of claim 1 wherein the beta isophorone and mesitylene removal zone comprises a distillation column, beta isophorone is removed at an intermediate level thereof, and the mesitylene is purged.

6. Method of claim 1 wherein the purifying is conducted by distillation.

7. Method of claim 1 wherein the catalyst is a synthetic anionic clay of the formula $(Mg_{1-x}Al_x)(OH)_2 \cdot xA$ where x is a number from 0.1 to 0.5, A is a univalent organic anion of the formula $RCOO^-$, where R is $C_nH_{2n+}$ and n is 0 to 4.

8. Method of claim 2 wherein the distillation column in the acetone removal zone is operated at a pressure of 300 mmHg to 20 psig.

9. Method of claim 4 wherein the distillation column in the mesityloxide removal zone is operated at a pressure of 100 mmHg to 20 psig.

10. Method of claim 5 wherein the distillation column in the beta isophorone and mesitylene removal zone is operated at a pressure of 20 mmHg to 5 psig.

11. Method of claim 1 wherein the purification step is conducted in a distillation column operated at a pressure of 10 mmHg to 5 psig.

12. Method of claim 1 wherein the acetone removed in the first treatment zone is recycled to the reactor.

13. Method of claim 1 wherein the mesityloxide removed in the mesityloxide removal zone is recycled to the reactor.

14. Method of claim 1 wherein the beta isophorone removed in the beta isophorone and mesitylene removal zone is recycled to the reactor.

15. Method of claim 1 wherein about 4% to about 20% of the initial reaction product comprises alpha isophorone.

16. Method of claim 8 wherein the pressure is 650 mmHg to 850 mmHg.

17. Method of claim 9 wherein the pressure is 400 mmHg to 600 mmHg.

18. Method of claim 10 wherein the pressure is 100 mmHg to 300 mmHg.

19. Method of claim 11 wherein the pressure is 50 mmHg to 100 mmHg.

* * * * *